(12) United States Patent
Reed et al.

(10) Patent No.: US 10,101,260 B2
(45) Date of Patent: Oct. 16, 2018

(54) OPTICS SYSTEM FOR A FLOW CYTOMETER

(71) Applicant: BECKMAN COULTER, INC., Brea, CA (US)

(72) Inventors: Timothy Reed, Boulder, CO (US); Michael M. Morrell, Wellington, CO (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 14/776,888

(22) PCT Filed: Mar. 12, 2014

(86) PCT No.: PCT/US2014/024840
§ 371 (c)(1),
(2) Date: Sep. 15, 2015

(87) PCT Pub. No.: WO2014/151049
PCT Pub. Date: Sep. 25, 2014

(65) Prior Publication Data
US 2016/0033386 A1 Feb. 4, 2016

Related U.S. Application Data

(60) Provisional application No. 61/793,771, filed on Mar. 15, 2013.

(51) Int. Cl.
*G01N 21/00* (2006.01)
*G01N 15/14* (2006.01)
(Continued)

(52) U.S. Cl.
CPC ..... *G01N 15/1434* (2013.01); *G01N 15/1459* (2013.01); *G01N 21/53* (2013.01);
(Continued)

(58) Field of Classification Search
CPC .... G01N 15/1459; G01N 21/53; G01N 21/64; G01N 15/1434; G01N 15/1436;
(Continued)

(56) References Cited

U.S. PATENT DOCUMENTS 5,090,808 A   2/1992  Ishikawa et al.
5,101,113 A *  3/1992  Hirleman, Jr. ..... G01N 15/0211
                                               250/574
(Continued)

FOREIGN PATENT DOCUMENTS

CN        1031422      3/1989
CN       101118208     2/2008
(Continued)

OTHER PUBLICATIONS

International Search Report for International Application No. PCT/US2014/024840 dated Jul. 7, 2014 (3 pages).
(Continued)

*Primary Examiner* — Jamil Ahmed
(74) *Attorney, Agent, or Firm* — Merchant & Gould P.C.

(57) ABSTRACT

A flow cytometer includes a flow nozzle, a light source, an optics system, and a sensor analyzer. The flow nozzle provides a fluid along a flow path. The light source generates a light beam that illuminates the fluid. The optics system collects light rays that are radiated from the light beam by the fluid and passes or blocks the light rays based at least in part on the radiation angles associated with the light rays.

7 Claims, 15 Drawing Sheets

(51) Int. Cl.
*G01N 21/53* (2006.01)
*G02B 19/00* (2006.01)

(52) U.S. Cl.
CPC ..... *G02B 19/0023* (2013.01); *G02B 19/0085* (2013.01); *G01N 2015/1447* (2013.01)

(58) Field of Classification Search
CPC ........ G01N 15/14; G01N 21/00; G01N 33/48; G01N 33/49; G01N 15/06; G02B 19/00; G02B 19/0023; G02B 19/0085
See application file for complete search history.

(56) References Cited

U.S. PATENT DOCUMENTS

| | | | |
|---|---|---|---|
| 5,125,737 A * | 6/1992 | Rodriguez | G01N 15/1459 356/338 |
| 5,540,494 A | 7/1996 | Purvis et al. | |
| 6,404,493 B1 | 6/2002 | Altendorf | |
| 7,283,223 B2 | 10/2007 | Fritz | |
| 7,324,194 B2 | 1/2008 | Roche | |
| 7,385,682 B2 | 6/2008 | Chu et al. | |
| 7,561,267 B2 | 7/2009 | Luo | |
| 8,094,299 B2 | 1/2012 | Wells et al. | |
| 2004/0189971 A1 | 9/2004 | Nagai et al. | |
| 2004/0189977 A1 | 9/2004 | Nagai et al. | |
| 2008/0024758 A1* | 1/2008 | Tabata | G01N 15/1434 356/39 |
| 2009/0287421 A1* | 11/2009 | Malachowski | G01N 15/1475 702/21 |
| 2010/0220315 A1* | 9/2010 | Morrell | G01N 15/1436 356/73 |

FOREIGN PATENT DOCUMENTS

| | | |
|---|---|---|
| EP | 0 316 885 | 5/1989 |
| JP | 01-132932 A | 11/2002 |
| JP | 2004-144839 A | 5/2004 |
| JP | 2008-32659 A | 2/2008 |
| JP | 2008-39605 A | 2/2008 |
| JP | 2011-521228 A | 7/2011 |
| JP | 2012-47464 A | 3/2012 |
| WO | WO 2014/144585 | 9/2014 |

OTHER PUBLICATIONS

International Written Opinion for International Application No. PCT/US2014/024840 dated Jul. 7, 2014 (6 pages).

* cited by examiner

OPTICS SYSTEM FOR A FLOW CYTOMETER

CROSS-REFERENCE TO RELATED APPLICATION(S)

This application is a National Stage of PCT International Patent application No. PCT/US2014/024840, which claims benefit of U.S. Patent Application Ser. No. 61/793,771, filed on 15 Mar. 2013, titled OPTICS SYSTEM FOR A FLOW CYTOMETER and which applications are incorporated herein by reference in their entireties. To the extent appropriate, a claim of priority is made to each of the above disclosed applications.

BACKGROUND

Flow cytometers are used to evaluate the content of a sample. The sample is introduced into a fluid stream which is then illuminated with a light beam. When the light beam enters the fluid, it interacts with the sample and light is scattered out from the fluid in various directions. Light is also absorbed by the sample and produces fluorescence. By evaluating the way that the light radiates from the fluid and produces fluorescent light, characteristics of the sample can be determined.

SUMMARY

In general terms, this disclosure is directed to an optics system for a flow cytometer. In one possible configuration and by non-limiting example, the optics system includes a filter mask that filters (e.g., blocks or passes) light radiated from a fluid stream based on an angle at which the light radiates from the fluid. Various aspects are described in this disclosure, which include, but are not limited to, the following aspects.

One aspect is an optics system of a flow cytometer, the optics system comprising: a collection optics assembly arranged and configured to be positioned adjacent a fluid flow path and aligned with a path of a beam from a light source to collect light rays radiated from the beam by the fluid, or by particles in the fluid, in the fluid flow path; a collimator arranged to receive the light rays from the collection optics assembly, wherein the collimator directs the light rays through a focus insensitive region in which positions of the light rays are independent of fluctuations in the position of the fluid flow path with respect to the collection optics assembly; and a filter mask positioned at the focus insensitive region to selectively filter the light rays based on radiation angles associated with the light rays.

Another aspect is a method of filtering radiated light in a flow cytometer using an optical system, the optical system including at least one optical path, the method comprising: generating a light beam with a light source; directing the light beam in a first direction into a fluid stream, wherein the fluid stream includes a fluid flowing along a fluid path and particles within the fluid; collecting light rays radiated from the fluid, or the particles within the fluid, wherein the light rays are radiated at deflection angles relative to the first direction; and selectively filtering the light rays with a filter mask based at least in part on the radiation angles of the light rays, wherein the filter mask is positioned at a location in the at least one optical path where the selective filtering of the light rays based at least in part on the radiation angles of the light rays is independent of movement of the fluid path toward or away from the collection optics.

A further aspect is a flow cytometer comprising: a flow nozzle configured to provide a fluid, the fluid moving along a fluid flow path; a light source configured to generate a light beam to illuminate the fluid; an optics system including: a collection optics assembly positioned adjacent the fluid flow path and aligned with the light beam path to collect light rays radiated from the light beam by the fluid, or particles in the fluid, in the fluid flow path; a collimator arranged to receive the light rays from the collection optics assembly, wherein the collimator directs the light rays through a focus insensitive region in which positions of the light rays are independent of fluctuations in a position of the fluid flow path with respect to the collection optics assembly; and a filter mask positioned at the focus insensitive region to selectively filter the light rays based on radiation angles associated with the light rays; and a sensor analyzer operable to receive and detect the light rays that pass through the filter mask.

DETAILED DESCRIPTION

Figure 1:
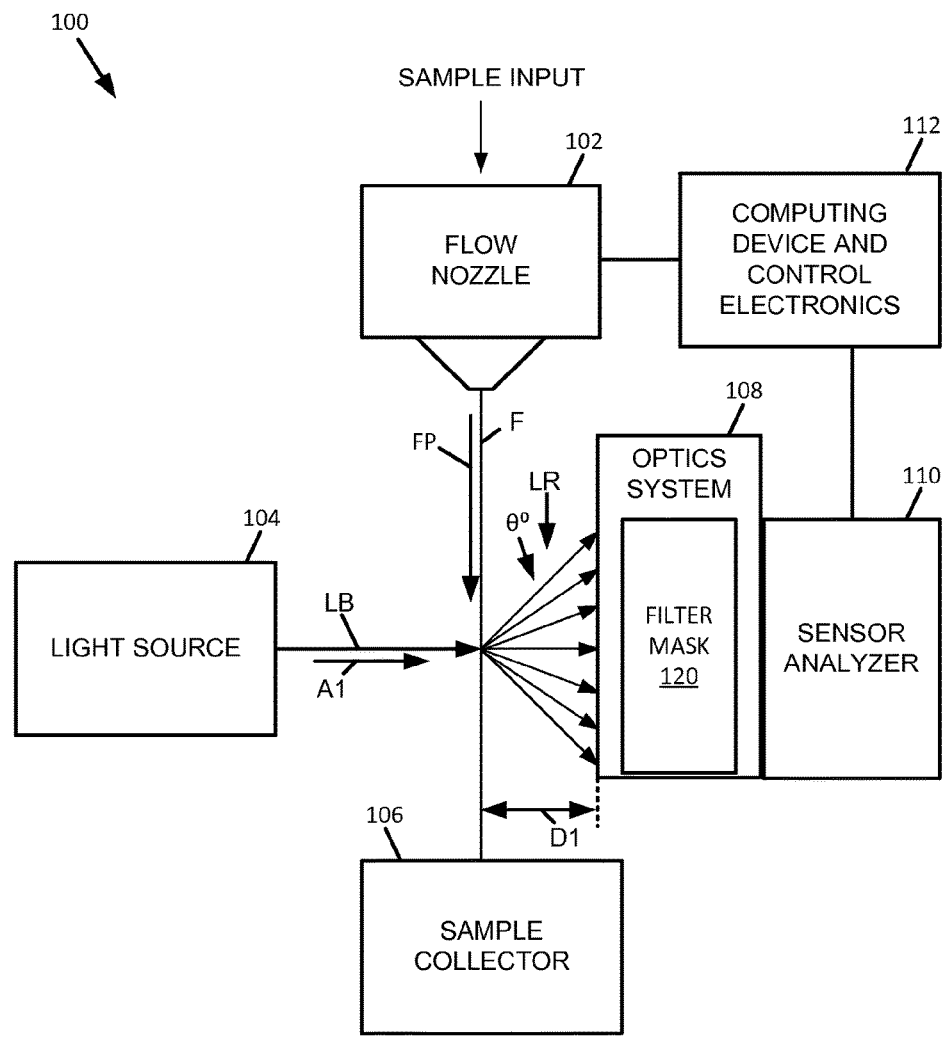
FIG. 1 is a schematic block diagram of an example flow cytometer according to the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a schematic block diagram of an example flow cytometer 100. In this example, the flow cytometer 100 includes a flow nozzle 102, a light source 104, a sample collector 106, an optics system 108, a sensor analyzer 110, and a computing device and control electronics 112. The optics system 108 includes a filter mask 120.

The flow nozzle 102 receives a sample containing particles for analysis by the flow cytometer 100. The flow nozzle 102 has a small aperture that permits only one or a small number of particles to pass through at a time, such as to arrange the particles so that they pass through the flow nozzle 102 in single file, for example. The sample is mixed with a sheath fluid, and the resulting fluid F containing the sample is directed along a flow path FP. Examples of flow nozzles 102 include a flow cell and a jet-in-air nozzle. In some embodiments, the flow cell includes a transparent body including a microscopically thin channel. The fluid stream containing the particles is directed by the walls of the channel along the fluid path extending through the flow cell and past the light source 104. In other embodiments a jet-in-air nozzle is used to eject the fluid stream along the fluid path. Hydrodynamic forces cause the fluid to flow in a continuous fluid stream and confine the particles as they pass the light source 104. Other embodiments utilize other flow nozzles 102.

The light source 104 generates a light beam LB. An example of the light source is a laser that generates a laser beam. The light beam LB is directed to the fluid path FP in a direction A1 where the light beam LB interrogates the fluid. Although the light beam LB is typically directed toward the fluid path FP by the light source 104 itself, the light beam LB can alternatively be directed by one or more optic devices, such as lenses, mirrors, prisms, and the like, in other embodiments after the light beam is emitted from the light source. Another example of a light source 104 is an arc lamp.

The fluid F is directed to a sample collector 106 after proceeding along the fluid path FP. In some embodiments, the sample collector 106 is a waste receptacle. In other embodiments, the sample collector 106 includes one or more storage receptacles. In another possible embodiment, the flow cytometer 100 is a sorting flow cytometer, and the sample collector 106 operates to sort the particles in the fluid into multiple receptacles based on one or more detected characteristics of the particles.

When the light beam LB, enters the fluid F, at least some of the light rays LR are scattered (e.g., forward, side, or back) by the particles within the fluid. The example shown in FIG. 1 illustrates light rays LR that are forward-scattered. Additionally, some of the light is absorbed and emitted at a different wavelength as fluorescent light. The scattered and fluorescent light is then radiated from the fluid. A radiation angle θ (sometimes also referred to as a scatter angle) is the angle of a light ray LR relative to the direction A1 of the light beam LB after being radiated from the fluid F. Because the light beam LB includes many light rays LR that can be separately radiated in different directions, different light rays LR can be radiated in different directions—having different radiation angles θ—simultaneously. Forward-scattering (and fluorescence) is illustrated and described in more detail with reference to FIG. 2. Although FIG. 1 illustrates only a vertical radiation angle θ, the light rays LR can also be radiated in a horizontal dimension (i.e., in all three dimensions).

An optics system 108 is positioned adjacent the fluid path FP to receive the radiated light rays. In some embodiments, the optics system 108 includes a filter mask 120. The filter mask 120 is arranged and configured to block a first portion of the light rays LR having a first set of radiation angles θ and to pass a second portion of the light rays having a second different set of radiation angles θ. The positions of the first and second portions can be adjusted in various possible filter masks 120 to selectively block and selectively pass certain portions of the radiated light. Other types of filtering can also be performed by the first and second portions of the filter mask 120 in some embodiments, in addition to or instead of blocking and passing. One example of a filter mask 120 is illustrated and described in more detail with reference to FIGS. 2-3. Additionally, some embodiments include an adjustable filter mask 120, which can be adjusted manually or by a computing device either mechanically or electronically. An adjustable filter mask can include a mechanically adjustable element that can be physically moved to different positions. In other possible embodiments, the filter mask includes a device having an adjustable transparency, such as a liquid crystal display. Another possible embodiment utilizes a microelectromechanical (MEMs) mirror, for example.

As discussed above, at least a portion of the optics system 108 is typically arranged adjacent the fluid path FP. In the illustrated example, the optics system 108 is positioned a distance D1 away from the fluid path. Different embodiments can have different distances D1. Some embodiments have a distance in a range from about 10 mm to about 15 mm, for example.

It has been found, however, that the precise location of the fluid path FP within the flow cytometer 100 can move relative to the optics system 108. As a result, the distance D1 can vary slightly. For example, the position of the flow path FP at the location where the light beam LB intersects can move toward (−) or away (+) from the optics system 108 about 50 μm (e.g., in a range from about −50 μm to about 50 μm), increasing or decreasing the distance D1 accordingly. The motion in the stream can be caused by a variety of factors, such as by thermal changes in the flow cytometer, fluid instability, a pressure change, mechanical instability of the components, external vibrations, etc. The impact of such variation on the light rays LR as they pass through the optics system 108 is discussed in more detail herein.

After the light rays LR have passed through the optics system 108, they are detected by the sensor analyzer 110. The sensor analyzer 110 detects various characteristics of the light rays, such as one or more of the magnitude and position of the detected light, time duration of the light pulse as a particle traverses the light beam, the shape of the pulse, polarization, and wavelength.

The computing device and control electronics 112 interact with the sensor analyzer 110 to evaluate characteristics of the particles in the fluid. In some embodiments, the computing device 112 includes a display, and generates a user interface on the display to convey information regarding the characteristics of the particles in the fluid to a user. The computing device 112 typically includes at least one processing device (such as a central processing unit) and at least some form of computer readable media, such as computer readable storage media. Examples of computer readable media are described herein.

In some embodiments, the flow cytometer 100 is a sorting flow cytometer in which the computing device and control electronics 112 operate to sort particles into multiple different receptacles in the sample collector 106 based at least in part on the radiated light detected by the sensor analyzer 110. For example, drops of the fluid are selectively charged by the flow nozzle 102 prior to separation from the fluid stream at the flow nozzle 102 based on detected characteristics of the particles contained in the drops. The drops are then sorted into different receptacles by passing the drops through charged plates at the sample collector 106. The charged plates deflect the drops into the appropriate receptacles.

Figure 2:
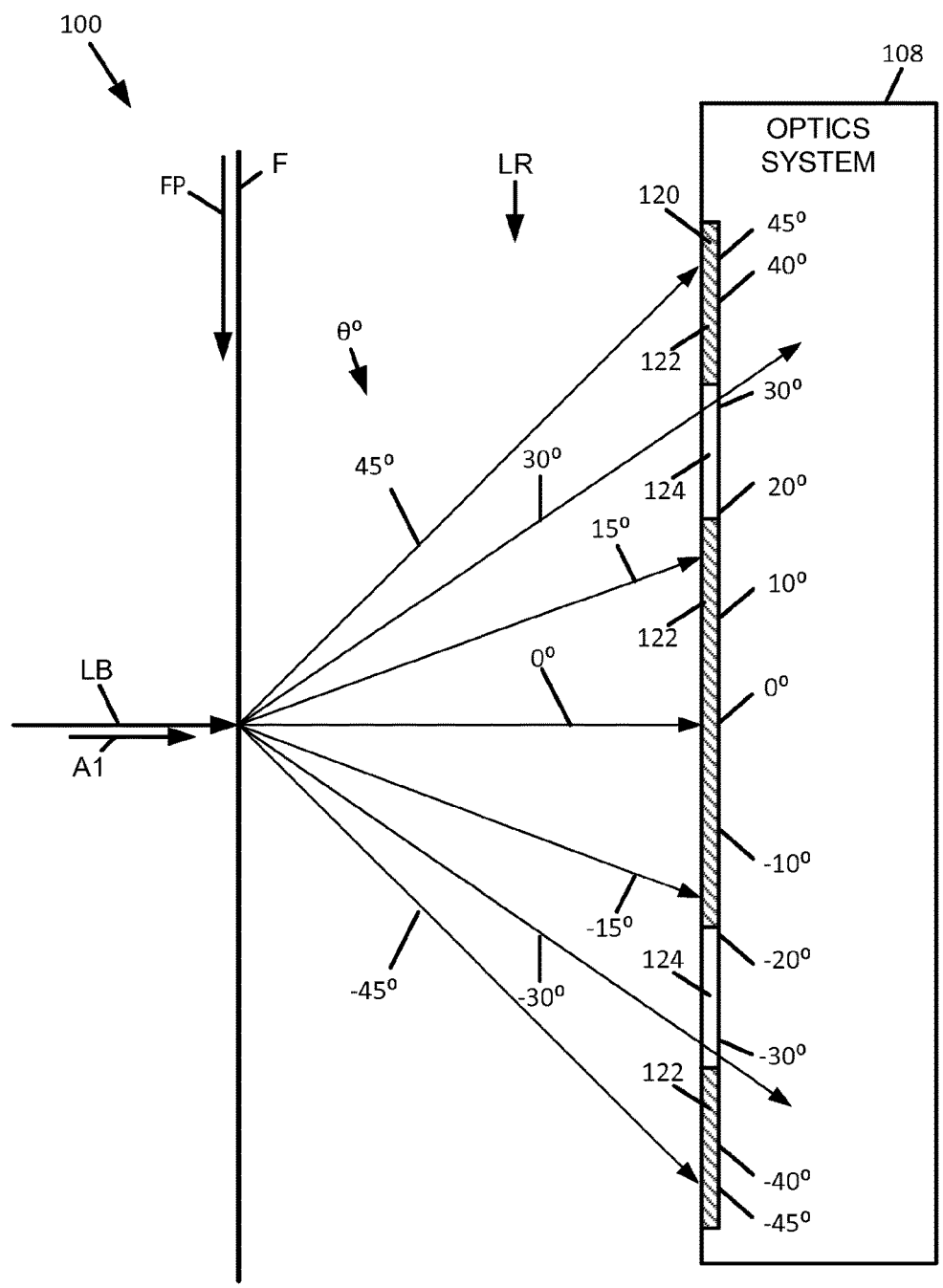
FIG. 2 is a schematic diagram illustrating a portion of the example flow cytometer shown in FIG. 1.

FIG. 2 is a schematic diagram illustrating a portion of an example flow cytometer 100, such as a portion of the flow cytometer 100 illustrated in FIG. 1. The illustrated portion of the flow cytometer 100 depicts the light beam LB, fluid F stream, light rays LR radiated from the fluid F stream, and the optics system 108. In this example a filter mask 120 is positioned at the front end of the optics system 108, adjacent the fluid stream (which is a focus insensitive region, as discussed in more detail herein).

When the light beam LB enters the fluid F, the fluid (and any particles contained in the fluid) cause the light rays LR to radiate in different directions (depicted by the radiation angles θ). The radiation occurs both vertically and horizontally. The vertical radiation is illustrated in FIG. 2, which illustrates light rays LR being vertically radiated between 45° (upward) and −45° (downward). The radiation also occurs horizontally, such as between −12° (left from the perspective of the light beam LB) and +12° (right). The radiation can also occur outside of these ranges, and some embodiments collect, filter, and/or evaluate light rays LR outside of these ranges.

It has been found, however, that not all of the light rays LR are equally informative when evaluating one or more characteristics of a sample. Therefore, a filter mask 120 can be used to selectively block certain portions of the light rays, while permitting the light rays of interest to pass through.

Figure 3:
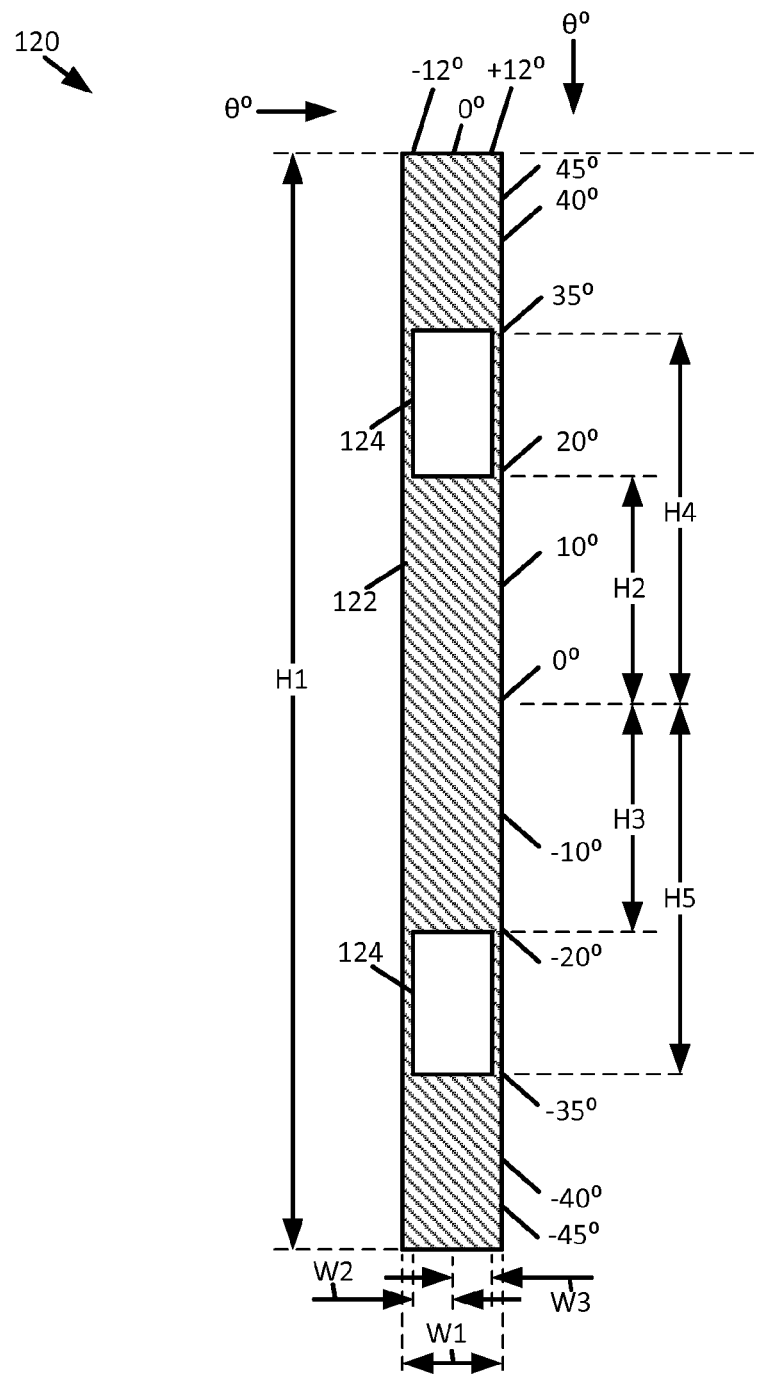
FIG. 3 is a front plan view of an example filter mask.

As one hypothetical example, suppose that the only light rays of interest were those having a radiation angle θ between +/−20° and +/−35°. A filter mask 120 could then be used as depicted in FIGS. 2-3. In this example, the filter mask 120 includes a body 122 that blocks the undesired portion of the light rays (such as those having radiation angles between −20° and +20°, and those having radiation angles greater than +/−35°. The filter mask 120 also includes apertures 124 formed in the body 122 at precise locations that permit light rays LR having radiation angles θ of interest (such as those having radiation angles θ between +/−20° and +/−35° to pass through.

The light rays that pass through the filter mask 120 are then collected by the optics system 108 and directed to the sensor analyzer 110 (FIG. 1), where the one or more characteristics of the sample are evaluated.

A benefit of the configuration shown in FIG. 2 is that precise filtering of light rays LR having particular radiation angles can be accomplished, limited primarily by the ability to precisely form apertures in the filter mask 120, and the ability to properly position the filter mask 120 with respect to the light beam LB direction A1.

Another benefit is that filter masks can be selected for use within the flow cytometer which have desired characteristics that are optimized for a particular application. For example, a first filter mask can be inserted into the optics system, which has a first set of characteristics that make it useful for a first application. The filter mask can then be removed and replaced with a different filter mask for a second application. In some embodiments, no changes need to be made to the optical system, other than to remove the filter mask and replace it with another filter mask having the desired characteristics. Additional examples are described herein.

FIG. 3 is a front elevational view of the example filter mask 120 shown in FIG. 2. In this example, the filter mask 120 includes a body 122 and apertures 124.

The body 122 of the filter mask 120 is arranged and configured to block certain portions of the radiated light rays LR from passing. For example, in some embodiments the surface is painted or formed of a material that will absorb most or all of the light rays LR. The filter mask 120 can be formed of a material such as plastic or metal, for example.

The filter mask 120 also includes apertures 124 formed in the body 122. The apertures 124 are positioned at particular locations in the body 122 to permit radiated light rays LR having certain radiation angles θ to pass through. In this example, the apertures are positioned to permit light rays LR having a nominal vertical radiation angle between +/−20° and +/−35° and a nominal horizontal radiation angle between −12° and +12° to pass through.

The actual physical dimensions of the filter mask 120 can be determined using a transfer function, which maps the radiation angles to the appropriate physical positions within the optics system. In some embodiments, the radiation angles are linearly related to the physical positions of the filter mask features. For example, when a distance D1 (shown in FIG. 1) between the flow path FP and the filter mask 120 is determined, and the desired radiation angles θ are known, the desired positions of the apertures in the body 122 can be computed using trigonometry. For example, center-most edges of apertures 124 are positioned a vertical distance H2,H3 away from the origin (the point at which the light beam LB is directed), where H2 and H3 are computed using the distance D1 and radiation angle θ (e.g., +/−20°). Similarly, the outer-most edges of apertures 124 are positioned a vertical distance H4,H5 away from the origin, where H4 and H5 are computed using the distance D1 and radiation angle θ (e.g., +/−35°). The horizontal edges of apertures 124 are positioned a horizontal distance W2,W3 from the origin, where W2,W3 are computed using the distance D1 and horizontal radiation angles (e.g., +/−12°).

In some embodiments, however, the transfer function may be non-linear, such as having a logarithmic, parabolic, or other non-linear relationship. In such embodiments, the transfer function can be determined according to the specific characteristics of the optics system to permit mapping between the radiation angles and the physical positions for desired features of the filter masks.

The overall dimensions (height H1 and width W1) are selected so as to block all undesired light rays LR from proceeding through the optics system 108. In this example, the height H1 and width W1 are selected for light rays having radiation angles between +/−45° vertical and +/−12° horizontal, and for a distance D1 away from the flow path FP.

The example illustrated in FIG. 3 shows apertures 124 having inner edges (e.g., at +/−20° and outer edges (e.g., at +/−35° that are straight and aligned with a constant vertical radiation angle. In another possible embodiment, one or more edges of apertures 124 are curved, such as along a constant radiation angle magnitude. Stated another way, to collect light rays that are radiated in a particular range of angles from the radiating particle, in some embodiments the apertures have inner and outer edges that are at constant radial distances from the interrogation point. In some embodiments, the inner and outer edges are curved arcs of circles centered on the origin, rather than being straight-edged. However, straight-edges can be used in some embodiments as an approximation of a curved shape, particularly when the width of the aperture is relatively narrow.

The filter mask 120 illustrated and described herein is provided as only one example of the many different filter masks that can be used in other embodiments. Filter masks 120 can be configured having any desired arrangement, to permit light rays associated with certain desired radiation angles to pass through, while blocking other light rays associated with undesired radiation angles. For example, near and far edges of blocking regions of the filter mask are curved (e.g., constant radial distances from the laser beam path) in some embodiments. Additional details regarding exemplary filter masks 120 that can be utilized in the optics systems 108 are described in U.S. Patent Application Ser. No. 61/798,548, titled RADIATED LIGHT FILTERING FOR A FLOW CYTOMETER, and filed on even date herewith, the disclosure of which is hereby incorporated by reference in its entirety.

Figure 4:
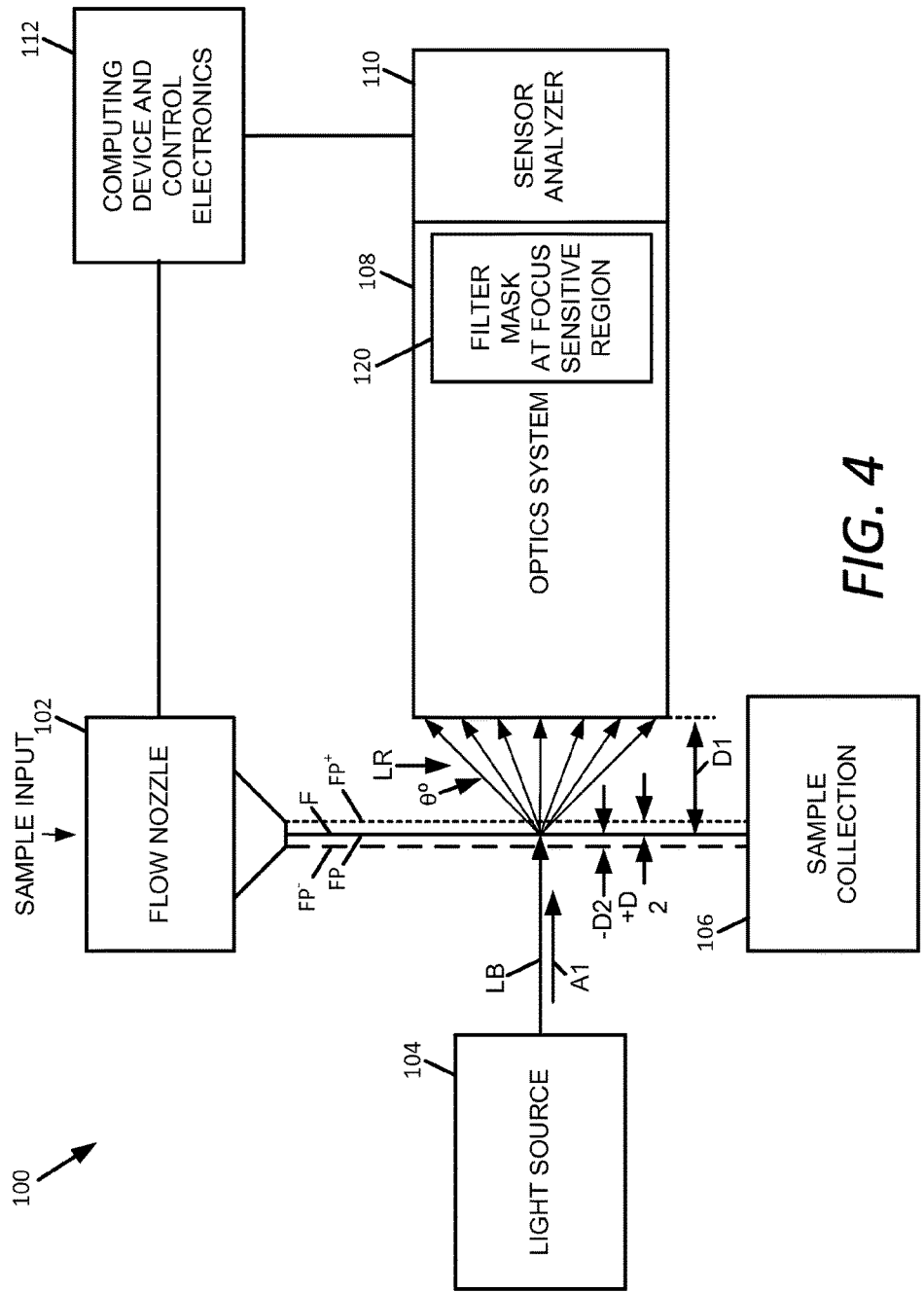
FIG. 4 is a schematic block diagram of another example flow cytometer according to the present disclosure.
Figure 5:
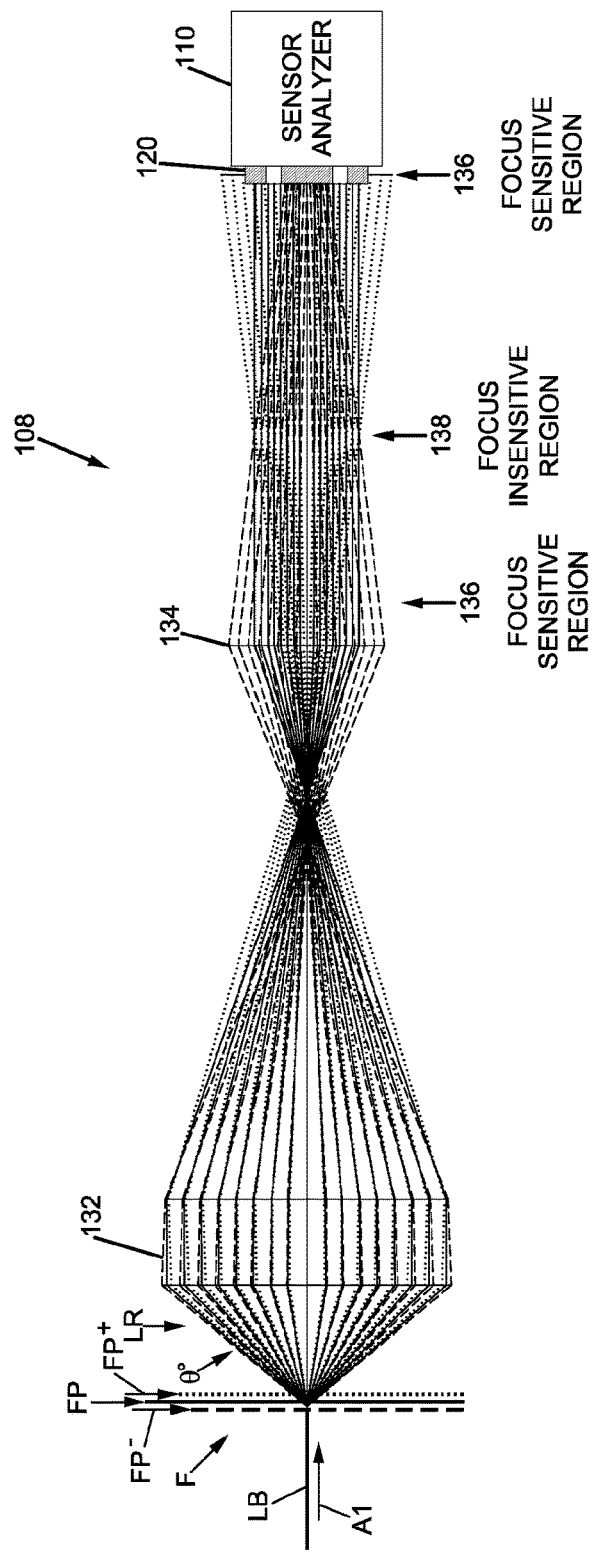
FIG. 5 is a schematic cross-sectional side view of an example optics system of the example flow cytometer shown in FIG. 4.
Figure 6:
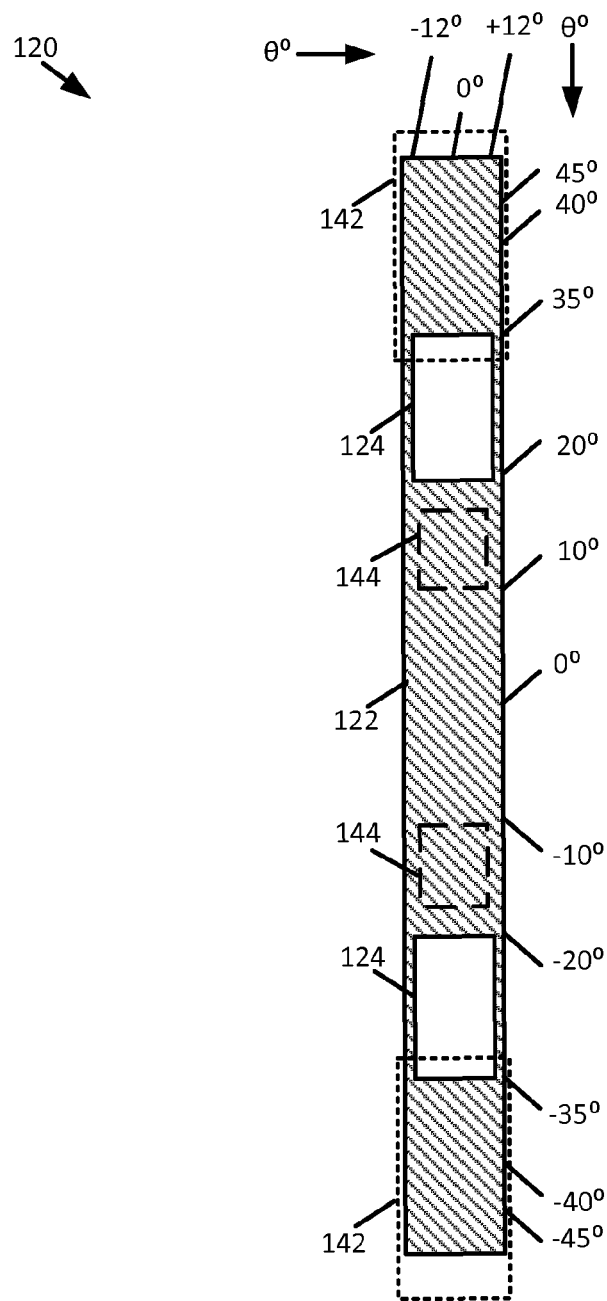
FIG. 6 is a front plan view of the example filter mask illustrating an incorrect filtering that occurs in this example when a flow path is shifted.

FIGS. 4-6 illustrate another example of a flow cytometer 100. In this example, the filter mask 120 is repositioned to move it further away from the fluid F flow path FP, by using the optics system 108 to collect the radiated light rays LR and directing them to the filter mask 120. This improves accessibility to the filter mask 120, for example. However, a drawback with this example is that the optics system 108 is sensitive to variations in the position of the flow path, as discussed in more detail below.

FIG. 4 is a schematic block diagram of another example flow cytometer 100. This example is similar to the example shown in FIG. 1, except that the filter mask 120 has been moved from the front of the optics system 108 (as in FIG. 1) toward the back of the optics system 108, as shown. A benefit of arranging the filter mask 120 at this position, for example, is that the filter mask 120 is more easily accessible. Additionally, the position of the filter mask 120 permits the use of additional stray light control features along the optical path to block light rays having unwanted/uncontrolled radiation angles before such light rays reach the filter mask 120.

Similar to that shown in FIG. 1, the flow cytometer 100 includes the flow nozzle 102, the light source 104, the sample collector 106, the optics system 108, the sensor analyzer 110, and the computing device and control electronics 112.

As noted above, however, the filter mask is positioned toward the back of the optics system 108 to permit improved ease of access to the filter mask 120, such as to allow the filter mask 120 to be more easily removed and replaced with a different filter mask 120. An example of the optics system 108 and filter mask 120 are illustrated and described in more detail with reference to FIG. 5.

In this example, the filter mask 120 is positioned at a focus sensitive position (such as region 136, illustrated in FIG. 5), as discussed in more detail herein.

In some embodiments the optics system 108 includes a collection optics assembly (such as shown in FIG. 5), which is arranged and configured to collect the light rays (LR) that are radiated from the fluid F. Accordingly, the collection optics assembly is selected and positioned so that a focal point of the collection optics assembly is located at the intersection of the fluid F flow path FP and the light beam LB.

It has been found, however, that the point at which the light beam LB intersects the fluid F is not constant, and varies over time. For example, the flow path or sample can move slightly toward the optics system 108 (as illustrated by flow path FP⁺) or slightly away from the optics system 108 (illustrated as flow path FP⁻). As one example, the flow path FP⁺ is shifted toward the optics system 108 a distance +D2, and the flow path FP⁻ is shifted away from the optics system 108 a distance −D2. Additionally, the position of a particle within the fluid stream can also shift. Although these variations may be minor (such as in a range from about +/−50 μm), these variations are magnified by the optics system 108, due to the flow path FP and/or particle moving in and out of focus.

Therefore, although this example works well to filter the light rays LR (using the filter mask 120) when the flow path FP is positioned at the focal point of the optics system 108, the example does not accurately filter the light rays LR when the flow path FP is positioned outside of the focal point (e.g., at FP⁺ or FP⁻) of the optics system 108.

FIG. 5 is a schematic cross-sectional side view of an example of the optics system 108, shown in FIG. 4, in which the filter mask 120 is arranged toward the back of the optics system 108. The magnitude of the light ray shifts illustrated in FIG. 5 (and some of the subsequent diagrams) is greatly exaggerated for ease of illustration and understanding.

In this example, the optics system 108 includes a collection optics assembly 132 and a collimator 134.

The collection optics assembly 132 is arranged and configured to collect the light rays LR after they pass through the fluid F. At least some of the light rays are scattered at radiation angles θ. The light rays LR are bent and directed toward the collimator 134. An example of a collection optics assembly 132 is an objective lens. The collection optics assembly 132 also includes one or more stray light control structures, such as a pinhole, in some embodiments. In some embodiments the pinhole comprises a mechanical structure having an aperture therein. The mechanical structure is non-transparent to block light, while the aperture permits light to pass therethrough. The stray light control structures are helpful in some embodiments to reduce the background signal to improve the ability of the system to detect light rays of interest.

The collimator 134 receives the light rays LR from the collection optics assembly 132. When the fluid F is arranged at the focal point of the collection optics assembly 132 (along flow path FP), the collimator 134 collimates the light rays LR so that they are substantially parallel to each other.

The light rays LR are then filtered by the filter mask 120. Because the relative positions of the light rays LR are maintained by the collection optics assembly 132 (i.e., highly scattered light rays are proportionately further from the center than unscattered light rays), the filter mask 120 can be used in the same way as illustrated and described with reference to FIG. 1 to filter out light rays associated with certain radiation angles, while permitting other light rays (associated with other radiation angles) to pass through. Those light rays that pass through the filter mask 120 are then detected by the sensor analyzer 110.

When the filter mask 120 is positioned in a focus sensitive region 136, however, the filter mask may not filter the light rays LR in the intended manner when the position of the flow path FP moves away from the focal point of the collection optics assembly 132, causing the flow path to move out of focus.

To illustrate this, FIG. 5 schematically depicts the optical paths of the light rays LR originating from three different positions of the fluid F flow path FP. The first optical path (illustrated with solid lines) occurs when the flow path FP is at the focal point of the collection optics assembly 132. The second optical path (illustrated with dotted lines) occurs when the flow path FP is shifted toward the collection optics assembly 132 along flow path FP⁺. The third optical path (illustrated with dashed lines) occurs when the flow path FP is shifted away from the collection optics assembly 132 along flow path FP⁻.

As can be seen, although the change in position between the flow path FP and flow paths FP⁺ or FP⁻ may be quite small (such as approximately +/−50 μm), the difference is greatly magnified by the optics system 108. When the light rays LR arrive at the filter, the positions of the light rays are significantly shifted from the desired locations. For example, the light rays originating from FP⁺ are shifted outward from the origin, while the light rays originating form FP⁻ are shifted inward toward the origin. The result, illustrated more clearly in FIG. 6, is that the filter mask 120 may allow light rays associated with undesired radiation angles to pass through, and may block light rays associated with desired radiation angles, when the flow path is shifted from the focal point of the collection optics assembly 132.

FIG. 5 also shows a region 138 in the optical path that is focus insensitive, in contrast to the focus sensitive region 136. This focus insensitive region 138 is utilized in the example flow cytometers 100 illustrated and described in more detail with reference to FIGS. 7-15.

FIG. 6 is a front plan view of the example filter mask 120, illustrating the incorrect filtering that occurs when the flow path is shifted from the focal point of the collection optics.

As discussed above, when the flow path FP is correctly positioned at the focal point of the collection optics, the desired light rays correctly align with the filter mask 120. As a result, the desired light rays pass through the apertures 124, while the undesired light rays are blocked by the filter mask 120.

When the fluid F is shifted toward the optics system 108 at flow path FP⁺, the optical path of the light rays LR is substantially shifted at the filter mask 120. For example, the desired light rays LR are shifted to region 142, represented by the dotted line. As can be seen, only a small portion of the desired light rays pass through the apertures 124, and many of the undesired light rays (those outside of regions 142) are permitted to pass through the apertures 124 of the filter mask 120.

Similarly, when the fluid F is shifted away from the optics system 108 at flow path FP⁻, the optical path of the light rays LR is substantially shifted from the desired position at the filter mask 120. For example, the desired light rays LR are shifted to region 144, represented by the dashed line. As can be seen in this example, all of the desired light rays are blocked by the filter mask 120, while undesired light rays are permitted to pass through the apertures 124 of the filter mask 120.

Figure 7:
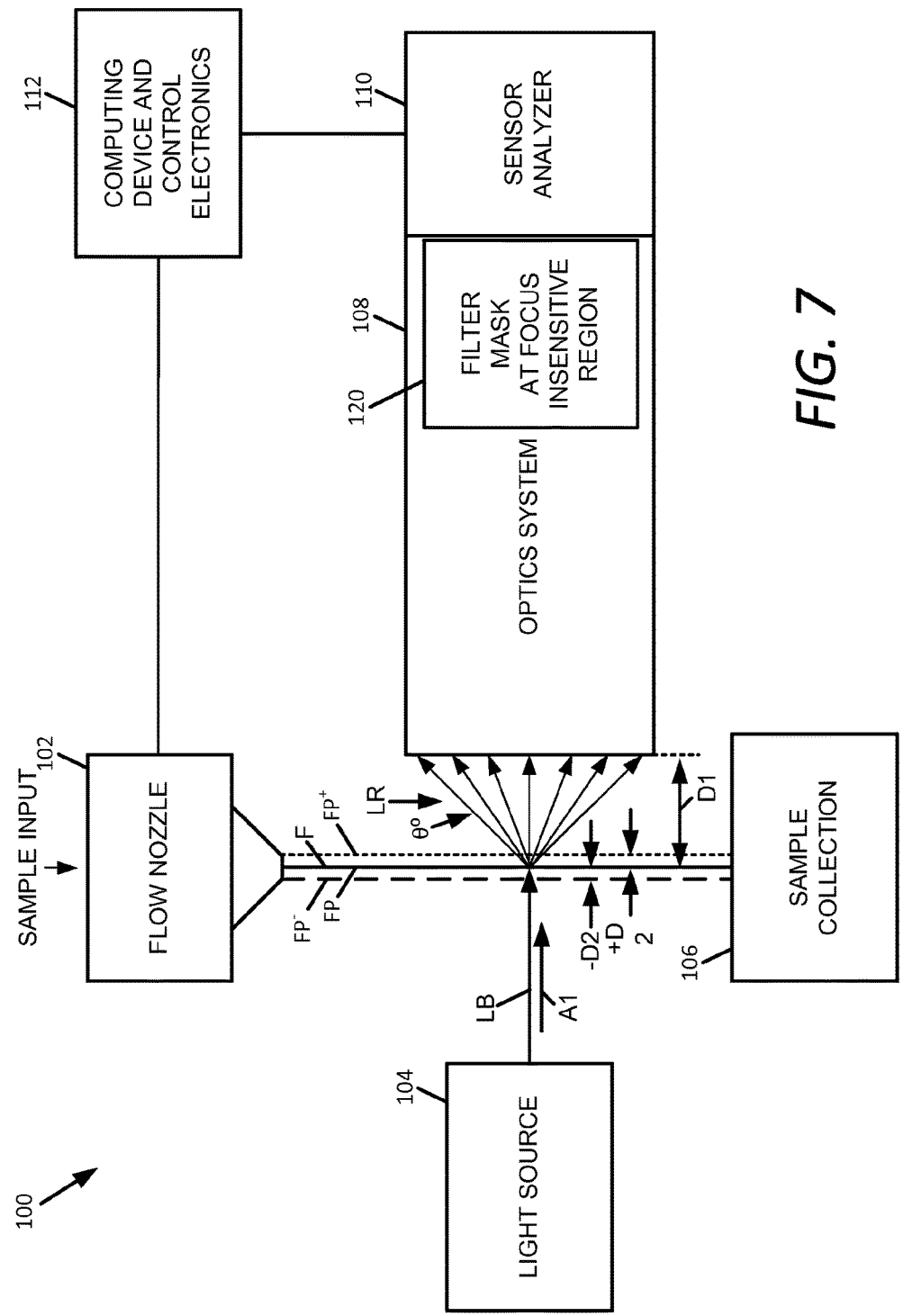
FIG. 7 is a schematic block diagram of another example flow cytometer according to the present disclosure.
Figure 8:
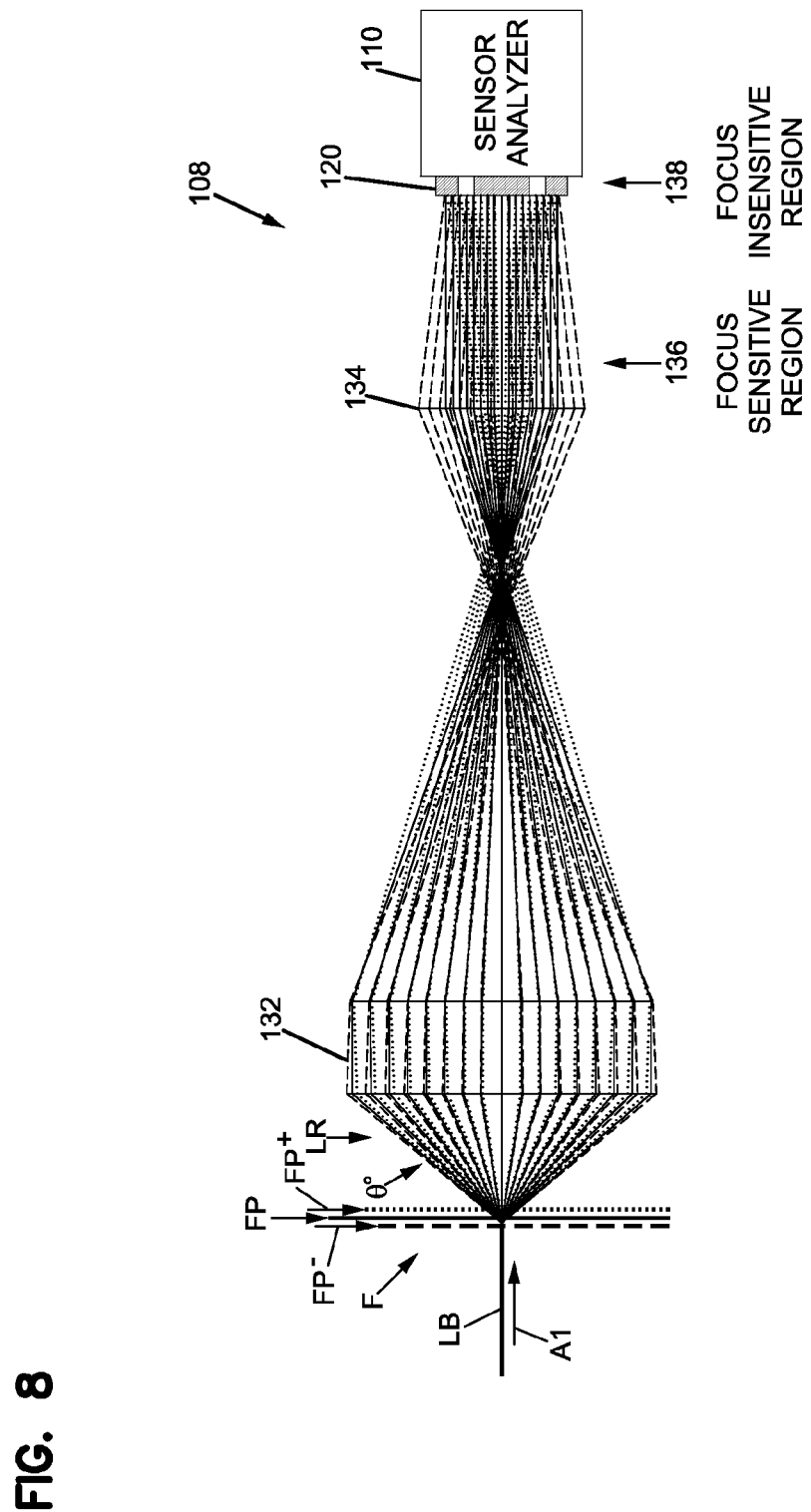
FIG. 8 is a schematic cross-sectional side view of an example of an optics system of the example flow cytometer shown in FIG. 7.
Figure 9:
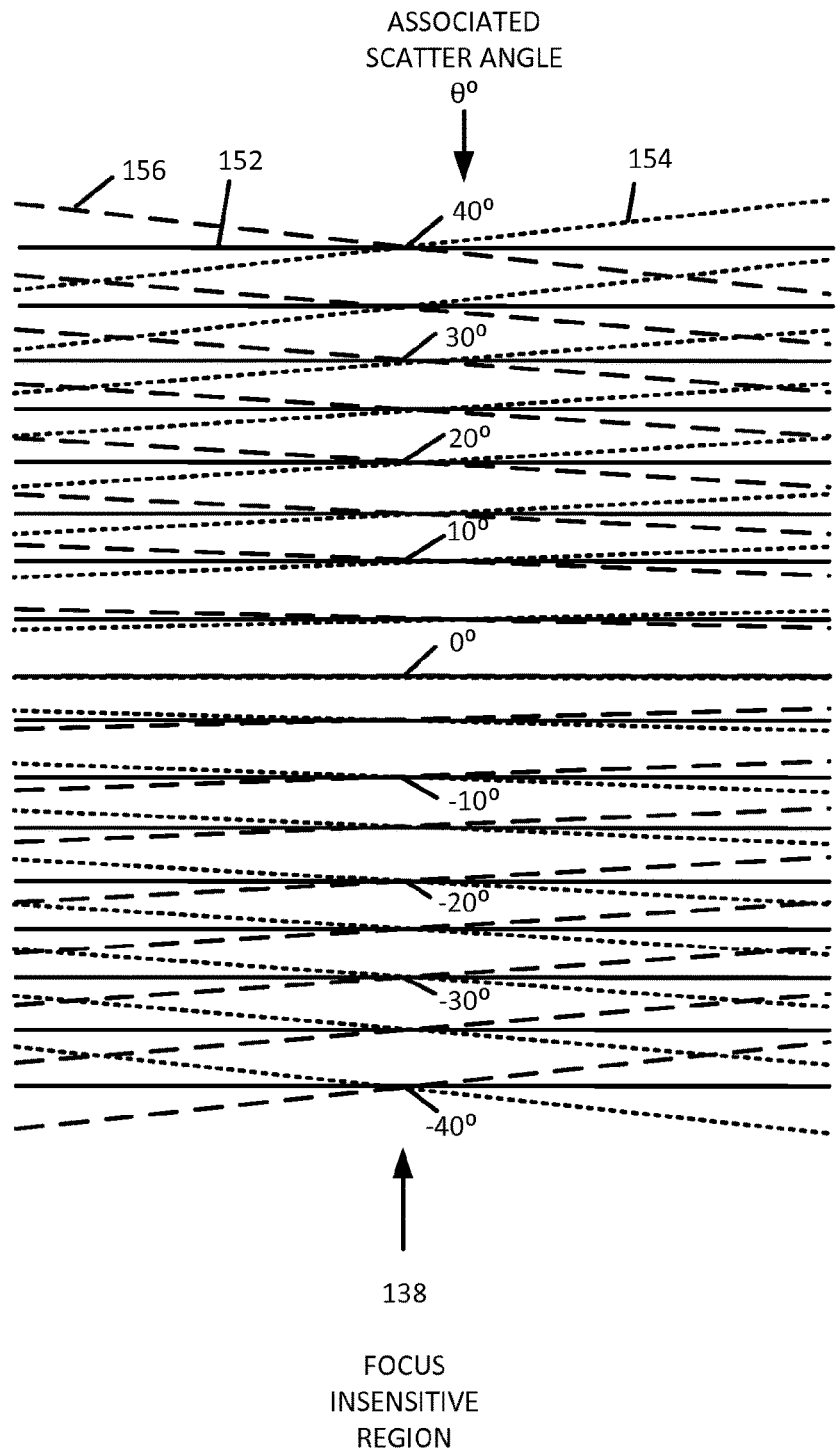
FIG. 9 is a schematic diagram illustrating a focus insensitive region of the example flow cytometer shown in FIG. 7.

FIGS. 7-9 illustrate another example of a flow cytometer 100, which overcomes the drawbacks of the prior examples.

FIG. 7 is a schematic block diagram of another example flow cytometer 100. This example is similar to the example shown in FIG. 4, except that the filter mask 120 is moved from a focus sensitive region 136 (shown in FIG. 5) of the optics system 108 to a focus insensitive region 138 of the optics system 108. Accordingly, the example flow cytometer 100 obtains the benefits of the example shown in FIG. 4, such as improved accessibility of the filter mask 120, while also overcoming the sensitivity to the position of the flow path FP.

Similar to the examples shown in FIGS. 1 and 4, this example of the flow cytometer 100 includes the flow nozzle 102, the light source 104, the sample collector 106, the optics system 108, the sensor analyzer 110, and the computing device and control electronics 112.

The optics system 108 includes a filter mask 120 arranged in the optical path. More specifically, the filter mask 120 is positioned at a focus insensitive region.

FIG. 8 is a schematic cross-sectional side view of an example of the optics system 108, shown in FIG. 7, in which the filter mask 120 is arranged at a focus insensitive region of the optics system 108.

As in the example shown in FIG. 5, this example of the optics system 108 also includes a collection optics assembly 132 and a collimator 134. The light rays are collected by the collection optics assembly 132 and are nominally collimated by the collimator 134.

FIG. 8 schematically depicts the optical paths of the light rays LR originating from three different positions of the fluid F flow path FP, in the same way as in FIG. 5. The first optical path is illustrated with solid lines, which occurs when the flow path FP is at the focal point of the collection optics assembly 132. The second optical path is illustrated with dotted lines, which occurs when the flow path FP is shifted toward the collection optics assembly 132 along flow path FP⁺. The third optical path is illustrated with dashed lines, which occurs when the flow path FP is shifted away from the collection optics assembly 132 along flow path FP⁻.

After the light rays pass through the collimator 134, the light rays in the first optical path are properly collimated. The light rays in the second optical path (dotted lines), however, are diverging, and the light rays in the third optical path (dashed lines) are converging.

Despite the different directions of travel of the light rays on the different optical paths, each of the optical paths intersects at the focus insensitive region 138. For example, the light rays associated with a radiation angle θ of 45° all intersect at the same point regardless of whether they originated at the flow path FP or shifted flow path FP⁺/⁻. This is true for light rays associated with each radiation angle.

Accordingly, by positioning the filter mask 120 at the focus insensitive region 138, the filter mask 120 can be used to precisely filter the light rays LR according to the associated radiation angles θ, even when the fluid F flow path FP is not at the focal point of the collection optics assembly 132.

In some embodiments, the optical systems used between the fluid path FP and the filter mask 120 are achromatic over the range of light wavelengths (colors) intended for use. Simple lenses have the property of chromatism. That is, they direct rays of different wavelengths of light (colors) in slightly different directions. This will change the angles of the rays exiting a lens, the location of its focal point, and the sizes of images of different wavelengths (colors). Accordingly, different wavelength light sources will produce different light paths, different locations of the focus insensitive region, and different patterns of the included and excluded angle on the filter mask at the focus sensitive regions, unless the optical system is specifically designed to correct for and reduce this effect.

In some embodiments, the flow cytometers 100 use multiple wavelengths of light sources so that the sample may be illuminated by different wavelengths of light. Thus, in some embodiments the optical system 108 is designed to be used with different wavelengths of light without changing its configuration, and therefore must behave the same (to within a specified tolerance) for all wavelengths of light over the intended range of use.

Multiple lens systems made of different types of glass can be designed to minimize this effect over a select range of wavelengths. Lenses or lens systems of this type are said to be achromatic (i.e., not chromatic) and are called achromats.

Some embodiments employ multiple lens systems that reduce the effects of chromatism at various points in the system.

For instance, the collector optics 132 are designed to be achromatic so that the light rays LR all focus to a focal point over the wavelengths (colors) of intended use.

Similarly, in some embodiments the collimator 134 is achromatic so that the rays exiting it are all nominally collimated, regardless of wavelength—otherwise different wavelengths would exit the collimator at different angles and strike the filter mask 120 at different locations.

FIG. 9 is a schematic diagram illustrating the focus insensitive region 138 in more detail. The diagram illustrates the light rays along three exemplary optical paths, including the first optical path 152, second optical path 154, and third optical path 156. The light rays in the first optical path 152 originated from the fluid path FP (shown in FIG. 7) at the focal point of the optics system 108. The light rays in the second optical path 154 originated from the fluid path $FP^+$, which is closer to the optics system 108 than the focal point. The light rays in the third optical path 156 originated from the fluid path $FP^-$, which is further from the optics system 108 than the focal point.

The light rays along the first optical path 152 are collimated. The light rays in the second optical path 154 are diverging. The light rays in the third optical path 156 are converging.

Despite the different paths, FIG. 9 illustrates how each of the optical paths 152, 154, and 156 associated with a given radiation angle θ, intersects at the focus insensitive region, regardless of where the light ray originated from (whether the fluid path FP, $FP^+$, or $FP^-$). Although FIG. 9 illustrates only the vertical dimension, the same is true in the horizontal dimension.

Because each of the light paths intersect at common locations, when the filter mask 120 is positioned at the focus insensitive region 138, the filter mask 120 will properly filter the light rays according to the associated radiation angles θ even when the fluid path is shifted from the focal point of the collection optics assembly 132. For example, the filter mask 120 can be used to block a first portion of the light rays, while permitting a second portion of the light rays to pass therethrough (e.g., light rays associated with radiation angles θ between 20° and 35° and between −20° and −35° for the example filter mask shown in FIG. 3).

Figure 10:
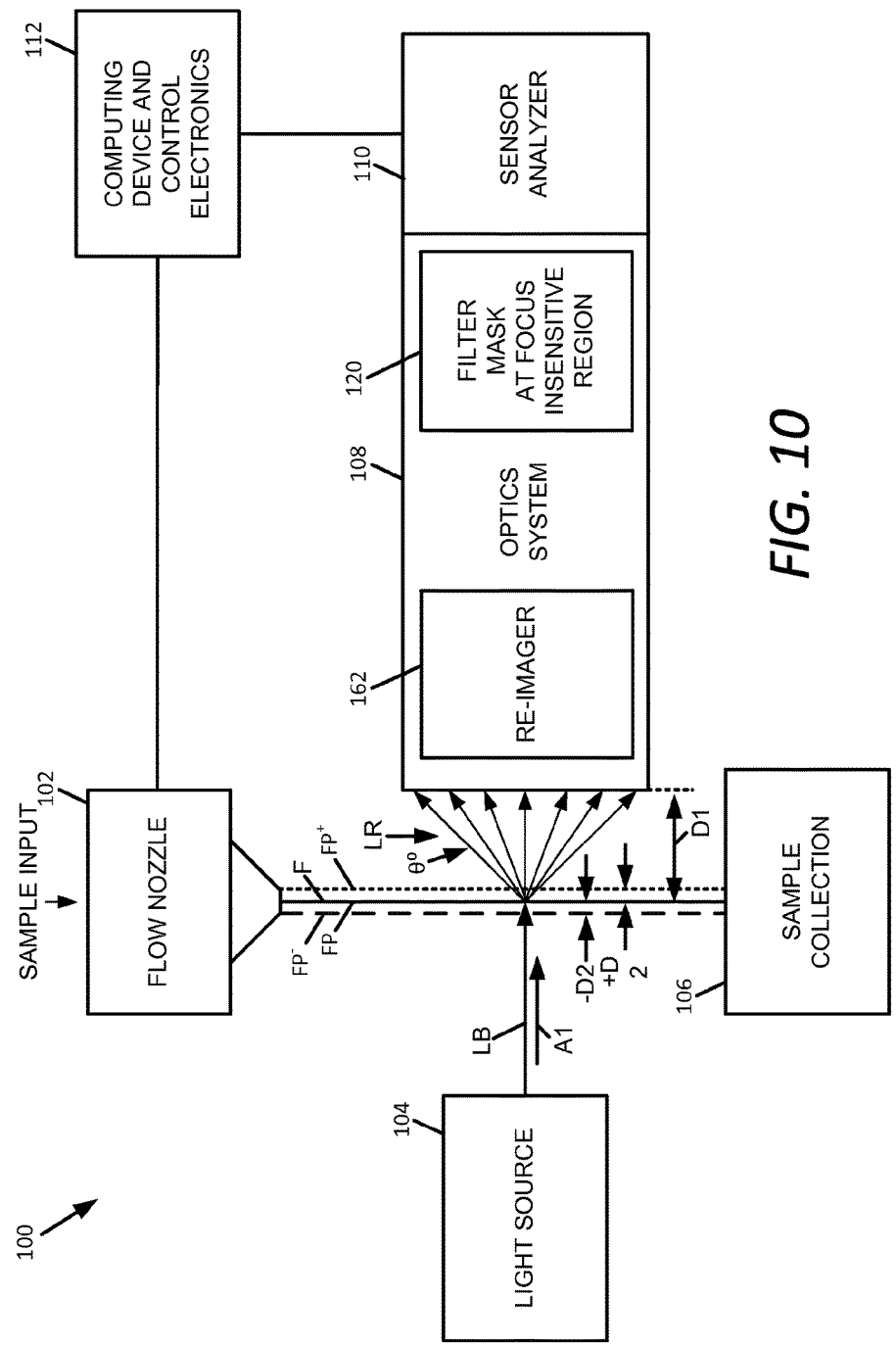
FIG. 10 is a schematic block diagram of another example of a flow cytometer according to the present disclosure.
Figure 11:
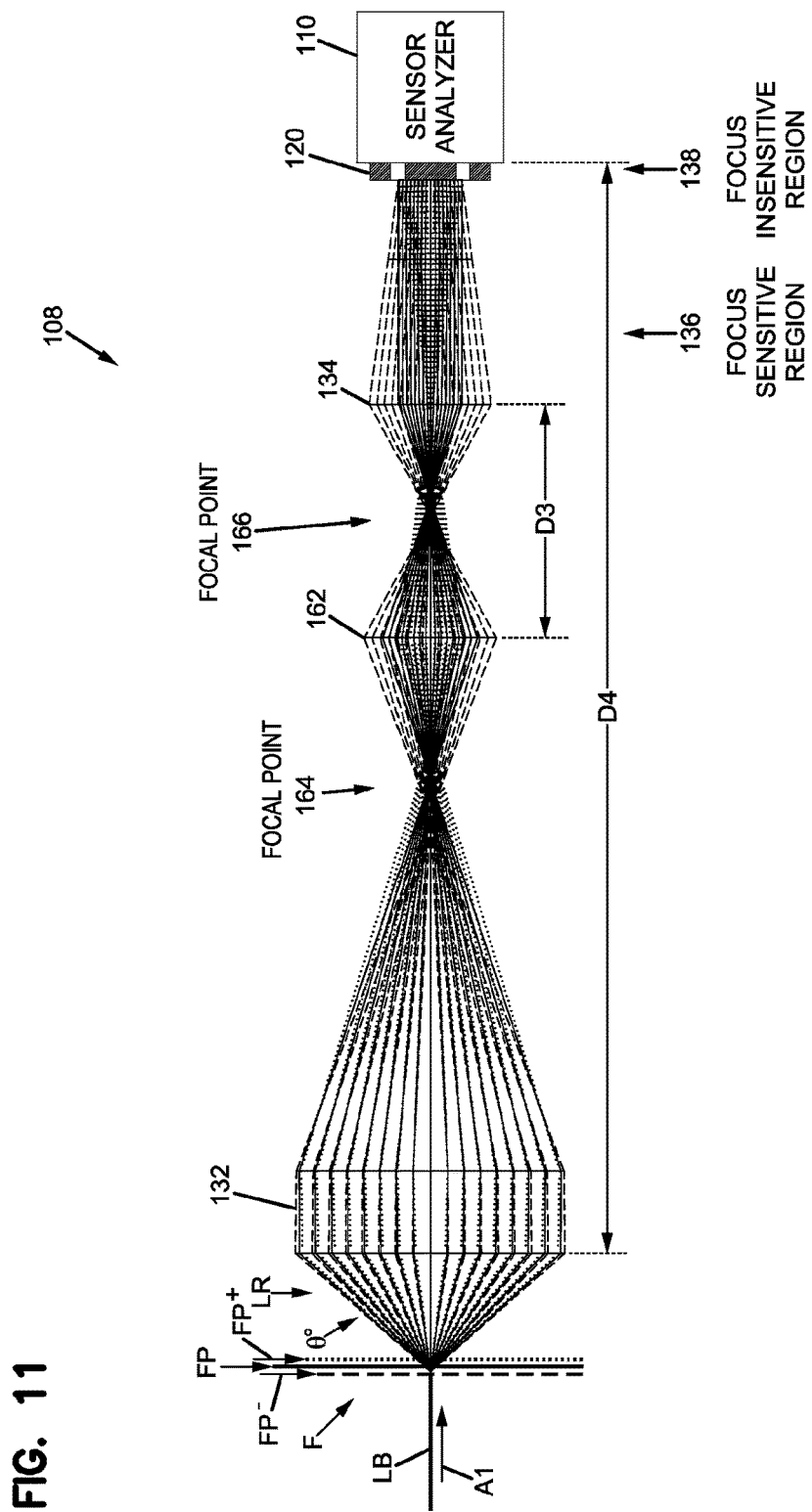
FIG. 11 is a schematic cross-sectional side view of an example of an optics system of the example flow cytometer shown in FIG. 10.
Figure 12:
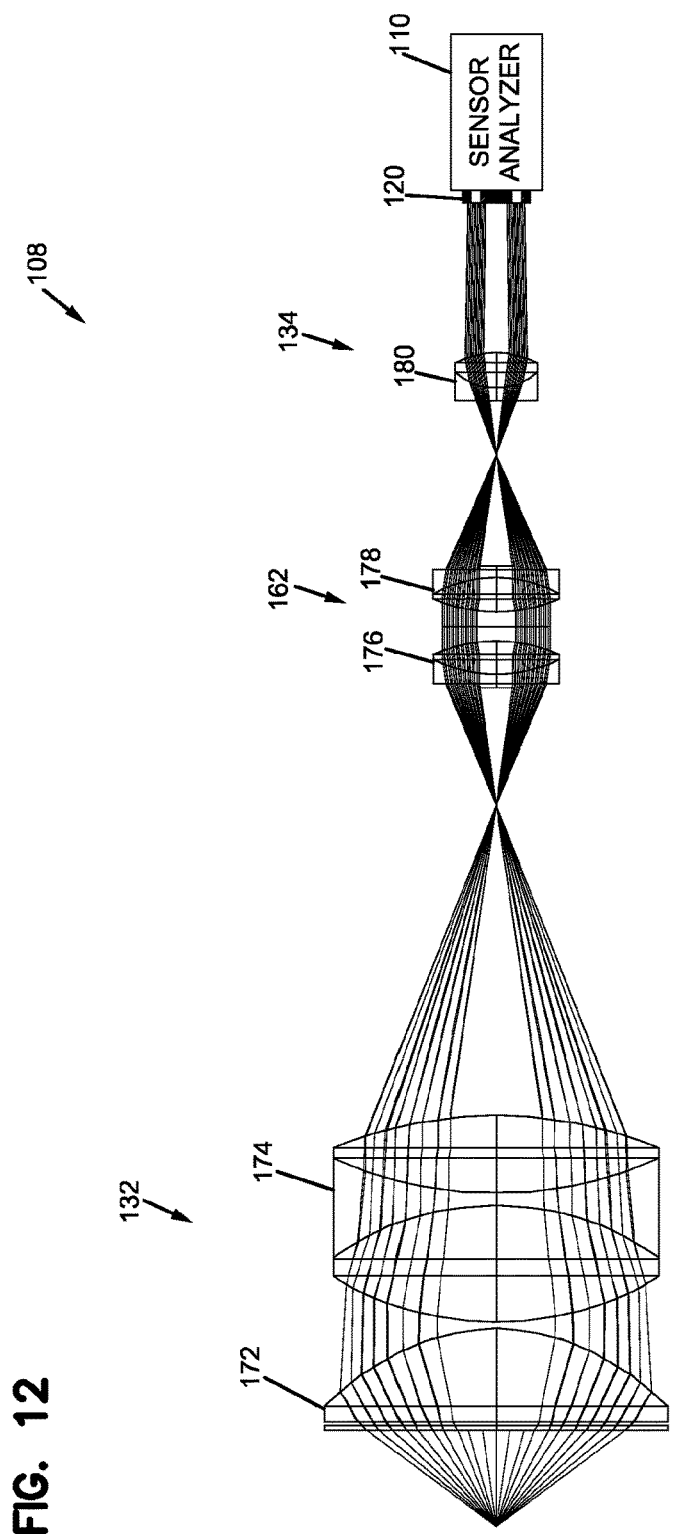
FIG. 12 is a cross-sectional side view of an example physical implementation of the example optics system shown in FIG. 11.

FIGS. 10-12 illustrate another example of a flow cytometer 100. In this example, the optics system 108 includes a re-imager. One advantage of using a re-imager is that it lengthens the optical path, allowing the filter mask 120 to be positioned even further away from the fluid path FP.

FIG. 10 is a schematic block diagram of another example of a flow cytometer 100. This example is similar to the example shown in FIG. 7, except for the addition of a re-imager 162 within the optics system 108. Accordingly, the example flow cytometer 100 obtains the benefits of the example shown in FIG. 7, such as reduced sensitivity to the position of the flow path FP, while also permitting relocation of the filter mask 120 (and some or all of the downstream components of the flow cytometer 100) to a more desirable location.

Similar to the examples shown in FIGS. 1, 4, and 7, this example of the flow cytometer 100 includes the flow nozzle 102, the light source 104, the sample collector 106, the optics system 108, the sensor analyzer 110, and the computing device and control electronics 112. The optics system 108 includes the re-imager 162 and the filter mask 120 at a focus insensitive region. A more detailed example of the optics system 108 is illustrated in FIG. 11.

FIG. 11 is a schematic cross-sectional side view of an example of the optics system 108, shown in FIG. 10, in which the optics system 108 includes a re-imager 162. More specifically, in this example the optics system 108 includes the collection optics assembly 132, the re-imager 162, the collimator 134, and the filter mask 120. The sensor analyzer 110 is arranged to receive and detect the light rays that pass through the optics system 108. The magnitude of the displacement of the light rays is greatly exaggerated in FIG. 11 for ease of illustration and understanding.

In this example, light rays are collected by the collection optics assembly 132 and directed to converge at a focal point 164. As shown, the position of the focal point 164 varies depending on the origin of the light rays LR (e.g., from flow path FP, $FP^+$, or $FP^-$). Beyond the focal point 164, the light rays begin to diverge. The re-imager 162 is positioned beyond the focal point 164 to receive the light rays LR from the collection optics assembly 132 at a position where the light rays LR are diverging.

The re-imager 162 receives the diverging light rays LR and redirects them so that they are once again converging toward a focal point 166. After converging at the focal point 166, the light rays again begin to diverge. In some embodiments, the re-imager 162 is achromatic, as discussed herein. The re-imager 162 is used to redirect the diverging light rays LR toward the focal point 166.

Although re-imagers are used, in some embodiments the quality of the images formed by the re-imagers is not important, provided that the radiation angles are preserved.

The collimator 134 is positioned beyond the focal point 166 to receive the light rays LR as they are diverging. The collimator 134 directs the light rays LR toward the filter mask 120.

After passing through the collimator 134, the light rays follow different optical paths depending on the origin of the light rays. However, all of the optical paths intersect at a focus insensitive region 138, and therefore the filter mask 120 is positioned at the focus insensitive region 138. The light rays that pass through the filter mask 120 are then received and detected by the sensor analyzer 110.

One advantage of this example of the optics system 108 is that inclusion of the re-imager 162 allows the overall length D4 of the optics system 108 to be shifted by a distance D3 without changing the overall sizes of the optical paths (e.g., when the sizes of the optical paths are the same at the re-imager 162 and the collimator 134). The distance D3 is twice the focal length of the re-imager 162, and therefore various distances D3 can be obtained by selecting a re-imager 162 having the desired focal length. As one example, the focal length of the re-imager is in a range from about 25 mm to about 50 mm, but other embodiments have other focal lengths. Additionally, the overall length of the optics system 108 can be adjusted by moving the re-imager closer or further from the focal point 164, and similarly by moving the collimator 134 closer or further from the second focal point 166.

Additionally, the use of re-imager 162 increases the width of the focus insensitive region 138. The increased width makes mechanical tolerancing easier within the flow cytometer 100, and reduces the sensitivity to small variations in the placement of the filter mask 120.

The overall optical path of the optics system 108 is illustrated as distance D4. In one example, the distance D4 is in a range from about 150 mm to about 250 mm. Other embodiments have other dimensions.

FIG. 12 is a cross-sectional side view of an example physical implementation of the example optics system 108 as schematically represented in FIG. 11.

As described above, this example of the optics system 108 includes the collection optics assembly 132, re-imager 162, collimator 134, and filter mask 120. The sensor analyzer receives and detects the light rays LR that pass entirely through the optics system 108.

In some embodiments, the collection optics assembly 132 is formed of multiple lenses, including lens 172 and lens 174. As one example, the lens 172 is a plano-aspheric lens having a flat front surface and a non-spherical rear surface. In some embodiments, the collection optics assembly is a multi-element microscope objective paired with a tube lens. An example of a suitable lens pair are the #58-373 and #54-774 available from Edmund Optics, Inc. of Barrington, N.J. In some embodiments that require greater collection angles, other lens pairs may be used, such as a higher NA microscope objective paired with a tube lens, or custom optics. An example of a suitable lens pair is the #59-880 and #54-774 available from Edmund Optics, Inc. of Barrington, N.J. In some embodiments, the optics assembly 132 includes four lens elements to bring the light rays LR to a single focal point, as shown, over all of the wavelengths (colors) of intended use. A flow cytometer having one or fewer wavelengths can alternatively utilize an optics assembly 132 that is less complex.

An example of the lens 174 is a triplet including three elements that are connected together by a fastener, such as adhesive. The first element has two convex surfaces, the second element has two concave surfaces, and the third element has two convex surfaces.

In some embodiments, the re-imager 162 is formed of multiple elements. In this example, the re-imager 162 includes two achromatic doublets 176 and 178. The doublet 176 includes a first element having a relatively flat (or slightly convex) front surface and a concave rear surface, and a second element having two convex surfaces. The elements are connected together to form the doublet 176. The doublet 178 is also made of two elements, which are simply arranged in the reverse order. An example of a doublet 176 suitable for the re-imager 162 is the Model No. AC127-019-A available from Thorlabs Incorporated of Newton, N.J. Although the doublets 176 and 178 are the same in some embodiments, other embodiments utilize doublets having different characteristics, such as having different focal lengths.

In some embodiments, the collimator 134 is formed of multiple elements. In this example, the collimator 134 is an achromatic doublet 180, similar to the doublet 176, though optionally having a different size and/or different characteristics. An example of a doublet 180 suitable for the collimator 134 is the Model No. AC080-010-A available from Thorlabs Incorporated of Newton, N.J.

Figure 13:
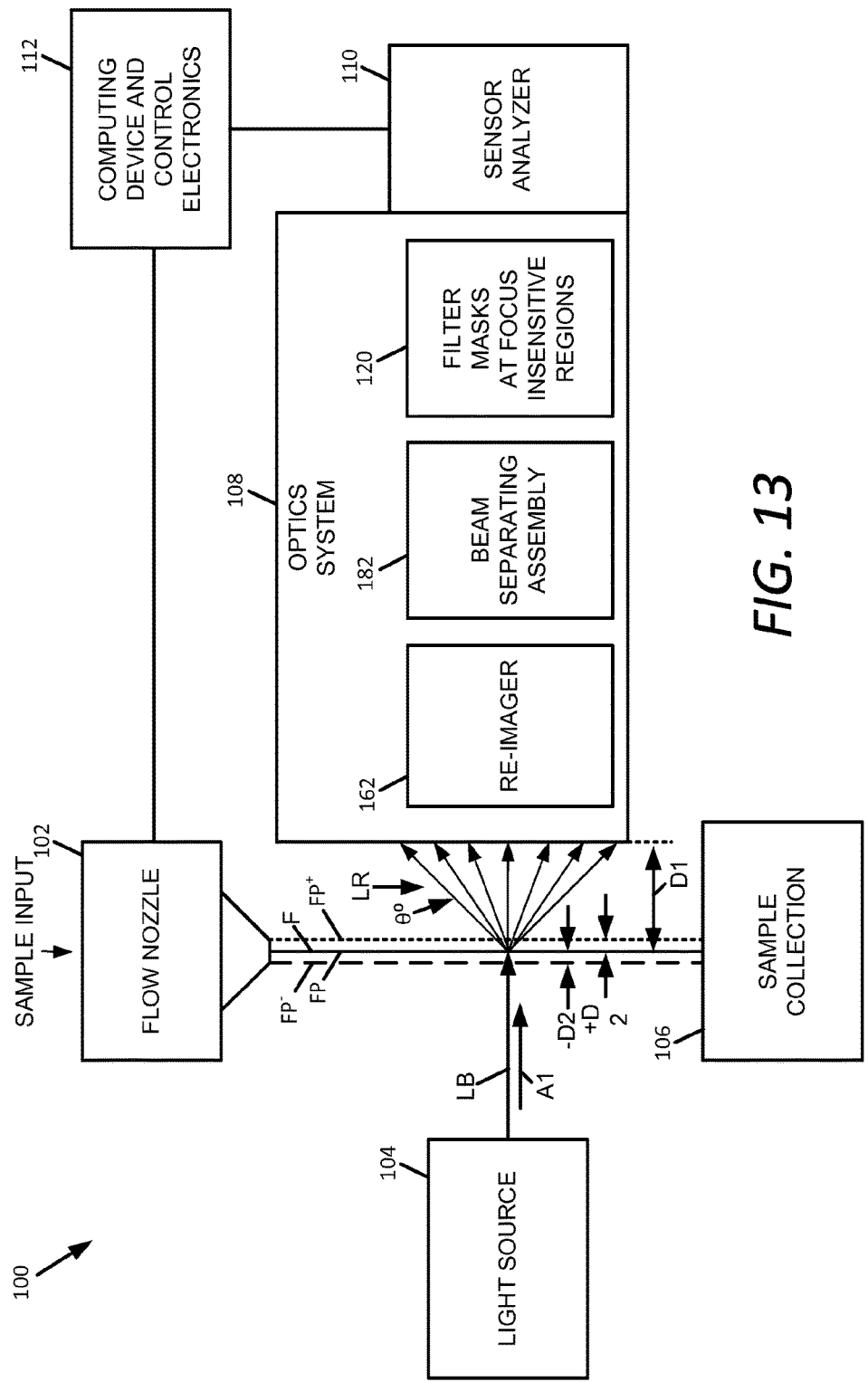
FIG. 13 is a schematic block diagram of another example of a flow cytometer according to the present disclosure.
Figure 14:
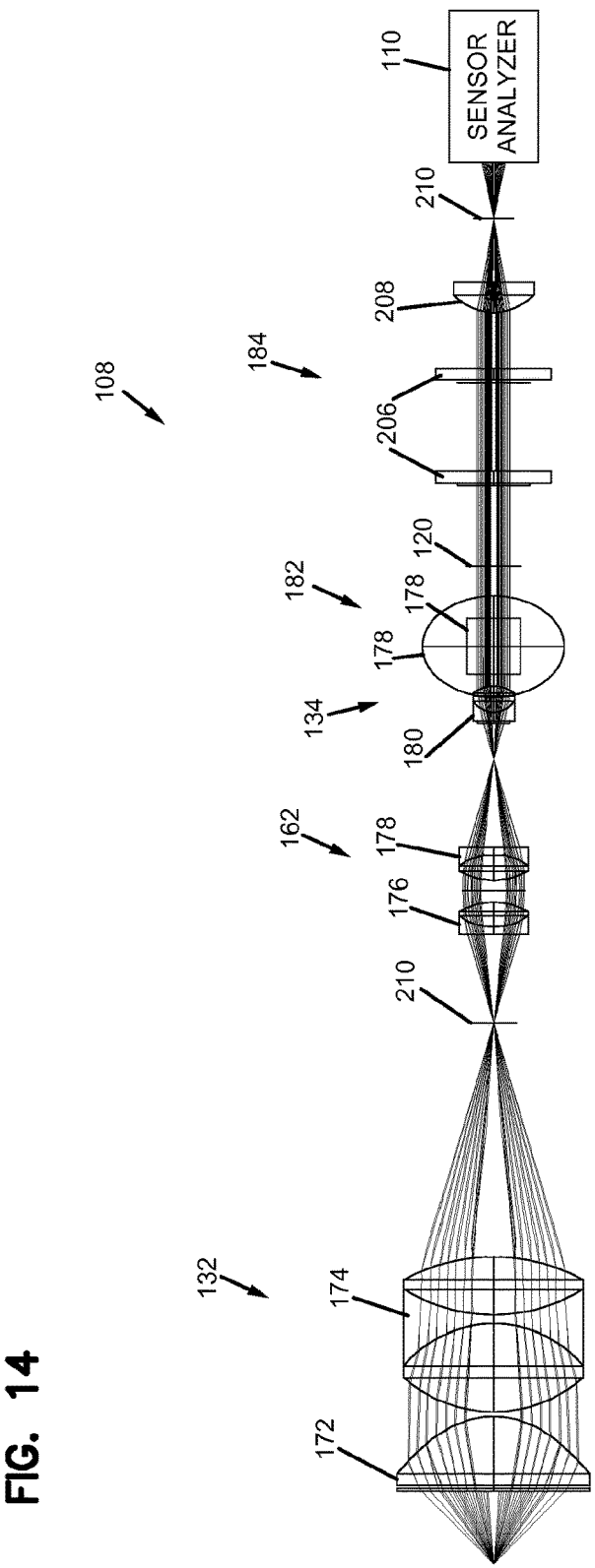
FIG. 14 is a cross-sectional side view of an example optics system of the example flow cytometer shown in FIG. 13.
Figure 15:
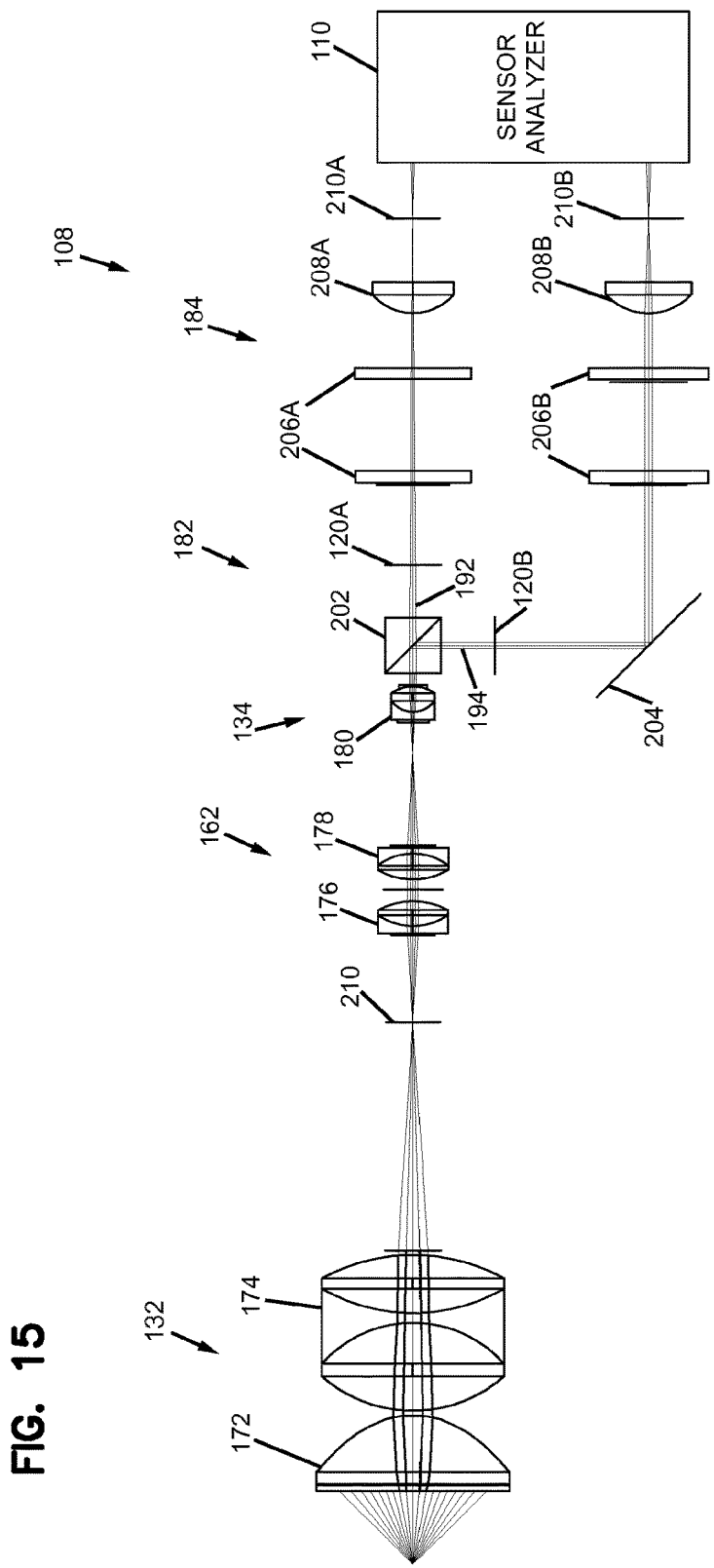
FIG. 15 is a cross-sectional top view of the example optics system shown in FIG. 14.

FIGS. 13-15 illustrate another example of a flow cytometer 100. In this example, the optics system 108 includes a beam separating assembly 182 that separates, or filters, the light rays into two or more beams. In addition, in some embodiments the optics system 108 includes two or more filter masks 120, for filtering the separated beams.

FIG. 13 is a schematic block diagram of another example of a flow cytometer 100. This example is similar to the example shown in FIG. 10, except for the addition of a beam separating assembly 182 in the optics system 108 to split the light rays LR into two or more beams, which permits, for example, the addition of multiple filter masks 120, or additional selection criteria such as polarization or wavelength.

Similar to the examples shown in FIGS. 1, 4, 7, and 10 this example of the flow cytometer 100 includes the flow nozzle 102, the light source 104, the sample collector 106, the optics system 108, the sensor analyzer 110, and the computing device and control electronics 112. The optics system 108 includes the re-imager 162, the beam separating assembly 182, and multiple filter masks 120 positioned at focus insensitive regions. A more detailed example of the optics system 108 is illustrated in FIGS. 14-15.

FIGS. 14-15 illustrate an example physical implementation of the example optics system 108 shown in FIG. 13. FIG. 14 is a cross-sectional side view of the optics system 108. FIG. 15 is a cross-sectional top view of the optics system 108.

In this example, the optics system 108 includes the collection optics assembly 132, re-imager 162, collimator 134, beam separating assembly 182, filter masks 120, as well as additional possible optical components 184.

The example physical implementations are similar to the example illustrated in FIG. 12. For example, in some embodiments the collection optics assembly 132 includes lens 172 and triplet 174, the re-imager 162 includes doublets 176 and 178, and the collimator 134 includes doublet 180.

Additionally, some embodiments include the beam separating assembly 182 that is arranged and configured to separate the light rays into two or more separate beams, such as beam 192 and beam 194 (shown in FIG. 15). In this example, the beam separating assembly 182 includes a beam splitter 202 and a mirror 204. The beam splitter 202 is positioned in the optical path of the optics system 108 and is configured such that a fraction of the light rays is reflected toward the mirror 204, forming beam 194, and the other fraction of the light rays is transmitted, forming beam 192, for example. In some embodiments, the mirror 204 is arranged to redirect the beam 194 toward the sensor analyzer, so that the beams 192 and 194 are parallel. In some embodiments the mirror 204 is omitted by arranging a sensor analyzer 110 along the path of beam 194. The light rays LR can be separated into additional beams, such as by using one or more additional beam splitters, if desired.

In another possible embodiment, the light rays are separated or filtered into one, two or more beams according to other characteristics, such as polarization or wavelength. In other words, by utilizing one or more beam splitters and one or more of the various filter masks, a wide variety of information regarding the particle within the fluid can be evaluated, such as by evaluation of wavelength, polarization, radiation angle, and time dependence, or other characteristics.

Each of the separate beams 192 and 194 can then be independently but simultaneously filtered and analyzed. In this example, each of the beams 192 and 194 is passed through a separate filter 120A and 120B. The filters 120A and 120B can be the same, or they can be different. For example, the filter 120A can be used to permit a selected portion of light rays to pass that are associated with certain radiation angles θ, and the filter 120B can be used to permit another selected portion of light rays to pass that are associated with other radiation angles θ. In this way the sensor analyzer 110 can evaluate multiple portions of the radiated light rays separately and simultaneously for the same portion of the fluid F.

Some embodiments include one or more additional optical components 184. Examples of the additional optical components include filter components 206, lenses 208, and aperture components 210.

The filter components 206 are provided in some embodiments to further filter the light rays before they are passed to the sensor analyzer. Examples of filter components 206 include spectral filters, neutral density filters, and polarizing filters.

The lenses 208A and 208B are provided to converge the light rays to a focal point to pass the light rays through aperture components 210A and 210B. The aperture components 210A and 201B are positioned at the focal points of the lenses 208A and 208B and are configured to block stray light from the sensor analyzer. Additional apertures components 210 can similarly be included at other focal points, such as any of the focal points 164 and 166 shown in FIG. 11.

Also, in some embodiments the path lengths are adjusted so that they are of equal length. For example, by adding or subtracting space after filter components 206 and before lenses 208, in the pseudo-collimated region, can cause the light getting to sensor analyzer 110 through the beams 192 and 194, to travel the same distance from the beam splitter 202. For instance, in some embodiments the distance between beam splitter 202 and the sensor analyzer 110 is increased (between filter components 206A and lens 208A) a distance equal to the distance between beam splitter 202 and mirror 204, so that the path lengths for beams 192 and 194 are equal. Alternatively, in another possible embodiment the distance between mirror 204 and sensor analyzer 110 can be reduced by the same distance.

Although the present disclosure is organized to introduce new concepts with reference to previously described examples, additional embodiments can be formed of various combinations of the concepts disclosed herein. For example, the beam separating assembly shown in FIGS. 13-15 can be included in the examples shown in FIG. 1, 4, 7, or 10. As another example, the re-imager shown in FIGS. 10 and 14 can be included in the examples shown in FIG. 1 or 4. These and other various combinations of features described herein can be made to result in additional possible embodiments that are within the scope of this disclosure.

As described herein, some embodiments of the flow cytometer 100 include one or more types of computer readable media. Computer readable media includes any available media that can be accessed by the computing device 112. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 112. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

In some embodiments, the term "substantially" refers to a deviation of less than 5%. In other embodiments, the term refers to a deviation of less than 1%. Yet other embodiments have a deviation of less than 0.1%. Other embodiments have other magnitudes of deviation.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A sorting flow cytometer comprising:
    a flow nozzle configured to provide a fluid that includes particles, the fluid moving along a fluid flow path, wherein the flow nozzle includes an aperture that permits only one or a small number of the particles to pass through at a time;
    a light source configured to generate a light beam to illuminate the fluid;
    an optics system including:
        a collection optics assembly positioned adjacent the fluid flow path and aligned with the light beam path to collect light rays radiated from the light beam by the fluid, or the particles, in the fluid flow path;
        a collimator arranged to receive the light rays from the collection optics assembly, wherein the collimator directs the light rays through a focus insensitive region in which positions of the light rays are independent of fluctuations in a position of the fluid flow path toward and away from the collection optics assembly; and
        a filter mask positioned at the focus insensitive region to selectively filter the light rays based on radiation angles associated with the light rays; and
    a sensor analyzer operable to receive and detect the light rays that pass through the filter mask;
    at least two receptacles; and
    control electronics configured to sort the particles into the at least two receptacles based on one or more detected characteristics of the particles.

2. The flow cytometer of claim 1, further comprising a beam separating assembly positioned between the collimator and the filter mask that separates the light beam into at least two separate beams, and further comprising a second filter mask, wherein the filter mask and the second filter mask are positioned along the two separate beams to independently filter the separate beams according to different criteria.

3. The flow cytometer of claim 2, wherein the separate criteria are selected from: different radiation angles, different wavelengths, and different polarizations.

4. The flow cytometer of claim 2, wherein a light ray having a first radiation angle is blocked by the filter mask and wherein another light ray having the same first radiation angle is passed by the second filter mask.

5. The flow cytometer of claim 1, wherein the optics system is configured to receive multiple different filter masks, including the filter mask, without requiring adjustment of the optics system for proper operation.

6. The flow cytometer of claim 2, wherein the filter mask filters the separate beams based on different radiation angles and the second filter mask filters the separate beams based on different wavelengths.

7. The flow cytometer of claim 2, wherein the filter mask filters the separate beams based on different radiation angles and the second filter mask filters the separate beams based on different polarizations.

* * * * *